US00PP10022P

United States Patent [19]

Zaiger et al.

[11] Patent Number: Plant 10,022

[45] Date of Patent: Sep. 9, 1997

[54] NECTARINE TREE "SPRING GLO"

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 613,686

[22] Filed: Mar. 11, 1996

[51] Int. Cl.[6] ..... A01H 5/00

[52] U.S. Cl. ..... Plt./41.1

[58] Field of Search ..... Plt./41.1

*Primary Examiner*—James R. Feyrer

*Assistant Examiner*—Melissa L. Kimball

[57] ABSTRACT

A new and distinct variety of nectarine, *Prunus persica*, tree; its novelty consists of the following unique combination of features that are desirable in a new variety:

1. Early maturity of medium size fruit.
2. Fruit with good flavor and eating quality.
3. Fruit with firm flesh, good handling and shipping quality.
4. Heavy and regular production of fruit.
5. Fruit with a high degree of attractive red skin color.
6. Fruit with a low winter chilling requirement of approximately 350 hours.
7. Having a vigorous, upright growth habit.

1 Drawing Sheet

ORIGIN OF THE VARIETY

The present variety of nectarine tree was originated in our experimental orchard located near Modesto, Calif., as a first generation cross between two selected seedlings with field identification numbers 31EB232 and 94ED118. The maternal parent (31EB232) originated from a cross of a seedling of open pollinated Ruby Gold Nectarine (U.S. Plant Pat. No. 3,101) with a selected seedling from a cross of Sun Red Nectarine (non-patented) with Tasty Gold Nectarine (U.S. Plant Pat. No. 5,623). The paternal parent (94ED118) originated as a selected seedling from a cross of Rhone Gold Nectarine (non-patented) with a high colored nectarine seedling of unknown parentage. A large group of these first generation seedlings were grown and maintained under careful and close observation, one low chilling seedling which is the present variety, having especially desirable fruit characteristics, was selected for asexual reproduction and commercialization.

ASEXUAL REPRODUCTION OF THE VARIETY

The new and distinct variety of nectarine tree was asexually reproduced by budding in our experimental orchard located near Modesto, Calif., which shows that all characteristics of the tree and fruit run true to form and are established and transmitted through succeeding asexual propagations.

SUMMARY OF THE VARIETY

The new and distinct variety of nectarine tree which is of large size, vigorous, upright growth and is a productive and regular bearer of medium size, early maturing, yellow flesh, clingstone fruit with good flavor and eating quality. The fruit is further characterized by being relatively uniform in size throughout the tree, having a high degree of attractive red skin color, and having firm flesh with good handling and shipping quality. The tree is further characterized by having a low winter chilling requirement of approximately 350 hours below 45° Fahrenheit and, in comparison to the low chilling May Glo Nectarine (U.S. Plant Pat. No. 5,245), the fruit is approximately 7 days earlier in maturity.

DESCRIPTION OF THE PHOTOGRAPH

The accompanying photographic illustration shows typical specimens of the foliage and fruit of the new nectarine tree, with the upper and lower surface of the leaves being shown, an exterior and sectional view of a fruit divided in the suture plane to show flesh coloration, pit cavity and a stone remaining in place. The photograph was taken at maturity (firm ripe) and the colors are as nearly true as reasonably possible in a color representation of this type.

DESCRIPTION OF THE VARIETY

The following is a detailed botanical description of the new and distinct variety of nectarine tree, its flowers, foliage and fruit as based on observations of specimen grown near Modesto, Calif., with color definitions (except those in common terms) referenced to Reinhold Color Atlas by A. Kornerup and J. H. Wanscher.

Tree:
- *Size.*—Large.
- *Vigor.*—Vigorous.
- *Form.*—Upright.
- *Production.*—Productive.
- *Density.*—Medium dense.
- *Bearer.*—Regular.

Trunk:
- *Size.*—Medium to large.
- *Surface.*—Medium shaggy.
- *Color.*—Brown to grayish brown (5-D-3) to (5-E-4).

Branches:
- *Size.*—Medium.
- *Texture.*—Smooth to medium rough.
- *Lenticels.*—Medium number. Large size.
- *Color.*—Light brown to brown (5-D-6) to (5-E-6).

Leaves:
- *Size.*—Medium to large. Average length 5½". Average width 1½".
- *Form.*—Lanceolate, pointed.
- *Margin.*—Crenate.
- *Texture.*—Smooth.
- *Thickness.*—Medium.
- *Petiole.*—Medium length. Medium thickness.

*Glands.*—Reniform. Number varies from 1 to 4. Average number 2. Medium size. Located on upper portion of petiole and lower portion of leaf blade.

*Color.*—Upper surface — green to dark green (28-F-6) to (28-F-8). Lower surface — dull green to grayish green (28-E-5) to (28-E-7).

Flower buds:

*Size.*—Medium to large.

*Form.*—Plump.

*Length.*—Medium.

Flowers:

*Size.*—Large, showy.

*Pollen.*—Present, self fertile.

*Color.*—Pink.

*Blooming period.*—Date of first bloom: Feb. 20, 1994. Date of full bloom: Feb. 25, 1994. Varies slightly with climatic conditions.

Fruit:

*Maturity when described.*—Firm ripe.

*Date of first picking.*—May 21, 1994.

*Date of last picking.*—May 26, 1994.

*Size.*—Medium. Average diameter axially 2½". Average transversely in suture plane 2½".

*Form.*—Globose, nearly symmetrical.

*Suture.*—Shallow, extends from base to apex.

*Ventral surface.*—Nearly rounded.

*Apex.*—Varies from round to slight apical point.

*Base.*—Retuse.

*Cavity.*—Rounded, slightly elongated in suture plane. Average depth ⅜". Average breadth ¾".

Flesh:

*Ripens.*—Evenly.

*Texture.*—Firm.

*Juice.*—Moderate.

*Fibers.*—Few, small, tender.

*Aroma.*—Very little.

*Flavor.*—Good.

*Eating quality.*—Good.

*Amygdalin.*—Undetected.

*Color.*—Light yellow to yellow (3-A-5) to (3-A-7). Pit cavity, dull yellow to grayish yellow (3-A-2) to (3-A-5).

Skin:

*Thickness.*—Medium.

*Texture.*—Tough, tenacious to flesh.

*Tendency to crack.*—Very slight.

*Down.*—Wanting.

*Color.*—Yellow ground color (3-A-6) to (4-A-6). Overspread with red (9-C-8) to (9-D-8).

Stone:

*Type.*—Clingstone.

*Size.*—Medium to large. Average length 1⅜". Average width 1 1/16". Average thickness ⅝".

*Form.*—Varies from ovate to obovate.

*Base.*—Rounded.

*Sides.*—Equal to unequal.

*Apex.*—Usually pointed, varies from pointed to rounded.

*Surface.*—Irregularly furrowed toward apex, pitted toward base.

*Tendency to split.*—Slight.

*Color.*—Light brown to brown (6-B-4) to (6-D-4).

Use: Dessert.

*Market.*—Local and long distance.

Keeping quality: Good.

Shipping quality: Good.

The new and distinct variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct nectarine tree, substantially as illustrated and described, characterized by its large size, vigorous, upright growth and a productive and regular bearer of medium size, early maturing, yellow flesh, clingstone fruit with good flavor and eating quality; the tree is further characterized by having a low chilling requirement of approximately 350 hours, producing fruit with an attractive red skin color and has firm flesh with good handling and shipping quality, in comparison to the fruit of the May Glo Nectarine (U.S. Plant Pat. No. 5,245), the fruit is approximately 7 days earlier in maturity.

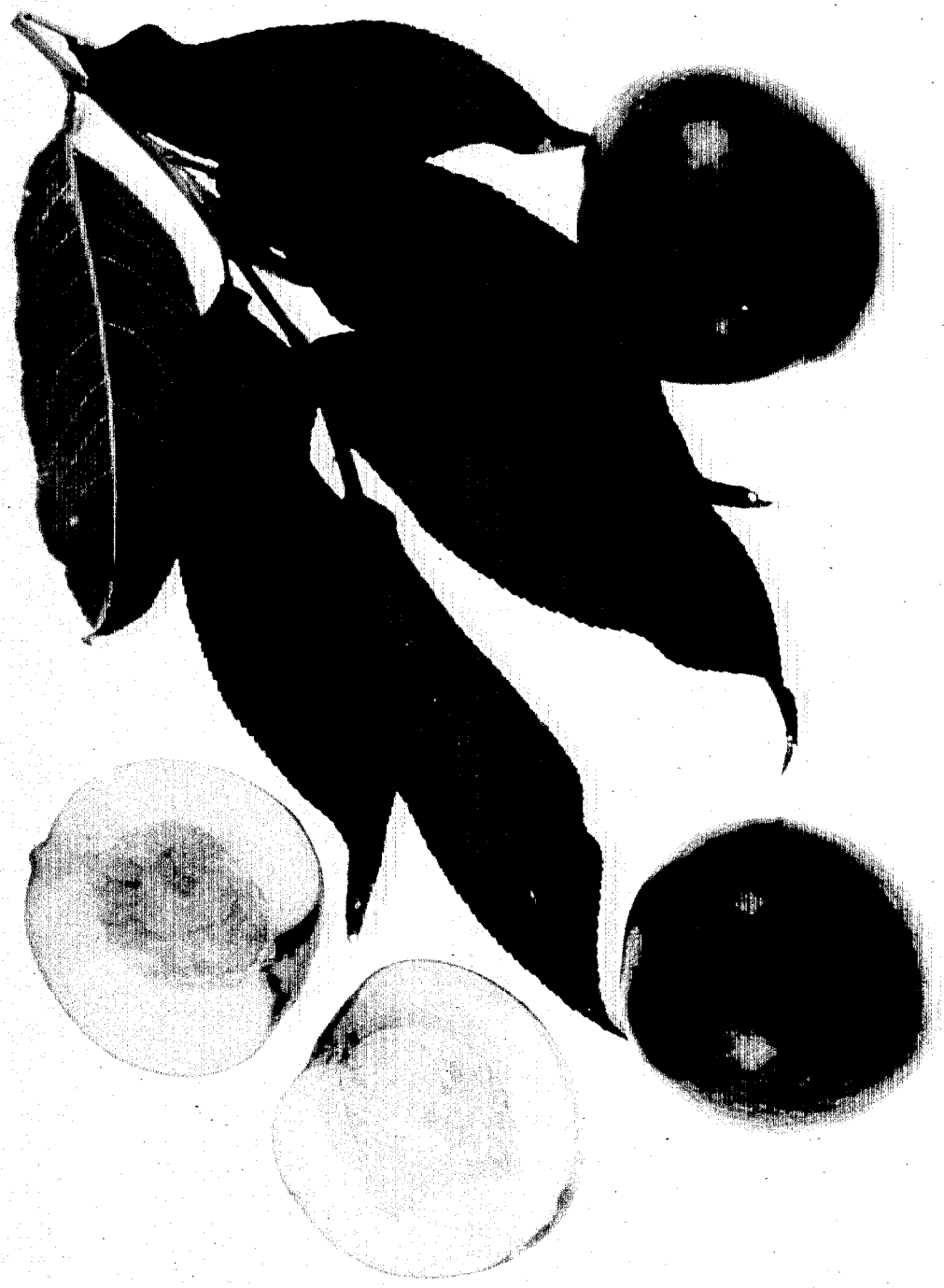

* * * * *